US012370047B2

(12) United States Patent  
Waechter-Stehle et al.

(10) Patent No.: US 12,370,047 B2  
(45) Date of Patent: Jul. 29, 2025

(54) SIGNAL-TRIGGERED INTERVENTIONAL DEVICE CONTROL

(71) Applicant: KONINKLIJKE PHILIPS N.V., Eindhoven (NL)

(72) Inventors: Irina Waechter-Stehle, Hamburg (DE); Rolf Jürgen Weese, Norderstedt (DE); Alexandra Groth, Hamburg (DE); Dirk Schaefer, Hamburg (DE); Arne Ewald, Hamburg (DE); Sven Kroenke, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 852 days.

(21) Appl. No.: 17/629,465

(22) PCT Filed: Jul. 28, 2020

(86) PCT No.: PCT/EP2020/071211  
§ 371 (c)(1),  
(2) Date: Jan. 24, 2022

(87) PCT Pub. No.: WO2021/018867  
PCT Pub. Date: Feb. 4, 2021

(65) Prior Publication Data  
US 2022/0240910 A1 Aug. 4, 2022

(30) Foreign Application Priority Data  
Jul. 30, 2019 (EP) .................................. 19188989

(51) Int. Cl.  
*A61F 2/24* (2006.01)  
*A61B 17/00* (2006.01)

(52) U.S. Cl.  
CPC ...... *A61F 2/246* (2013.01); *A61B 2017/00115* (2013.01); *A61B 2017/00132* (2013.01);  
(Continued)

(58) Field of Classification Search  
CPC .......... A61F 2/246; A61F 2/2442; A61F 2/24; A61B 34/20–2034/2065; A61B 2017/00694–2017/00703  
See application file for complete search history.

(56) References Cited

U.S. PATENT DOCUMENTS

| 9,855,384 B2 | 1/2018 | Cohen et al. |
| 2010/0022823 A1 | 1/2010 | Goldfarb |

(Continued)

FOREIGN PATENT DOCUMENTS

| JP | 2008220641 A | 9/2008 |
| WO | 2010075245 A2 | 7/2010 |

OTHER PUBLICATIONS

International Search Report and Written Opinion of PCT/EP2020/071211, dated Dec. 14, 2020.  
(Continued)

*Primary Examiner* — Alvin J Stewart (57) ABSTRACT

A system (SYS) for supporting a medical procedure, comprising an interface (IN) for receiving at least one medical input signal that describes a state of a target anatomy. A signal analyzer (SA) is configured to analyze the medical  
(Continued)

input signal to determine a time window for deployment of a cardio-vascular device (CL) to be deployed by a deployment.

14 Claims, 8 Drawing Sheets

(52) U.S. Cl.
CPC .............. *A61B 2017/00243* (2013.01); *A61B 2017/00703* (2013.01); *A61B 2017/00783* (2013.01)

(56) References Cited

U.S. PATENT DOCUMENTS

| | | | |
|---|---|---|---|
| 2010/0030061 A1* | 2/2010 | Canfield | A61N 1/372 600/413 |
| 2010/0114289 A1 | 5/2010 | Camus et al. | |
| 2010/0217283 A1 | 8/2010 | St. Goar | |
| 2012/0232386 A1 | 9/2012 | Mansi | |
| 2012/0307964 A1* | 12/2012 | Hall | A61B 6/03 378/8 |
| 2015/0223901 A1 | 8/2015 | Wei | |
| 2015/0366532 A1 | 12/2015 | Voigt | |
| 2017/0164893 A1* | 6/2017 | Narayan | A61B 5/024 |
| 2020/0397511 A1* | 12/2020 | Ishrak | A61F 2/2427 |
| 2021/0137634 A1* | 5/2021 | Lang | A61B 90/98 |
| 2024/0390145 A1* | 11/2024 | Sampson | A61F 2/2466 |
| 2025/0040894 A1* | 2/2025 | Johnson | A61B 5/1102 |

OTHER PUBLICATIONS

Gating Signal, Wikipedia, Nov. 6, 2013.
Bang-Bang Control—Wikipedia, Sep. 22, 2018.
Metreveli, Levan et al "New manoeuvres and timing of the latter for a Transcatheter mitral valve repair",—Experimental & Clinical Cardiology, vol. 20. 2013.
Pan, Jiapu et al, "A Real-Time QRS Detection Algorithm", IEEE Transactions on Biomedicla Engineering, vol. 32, No. 3, Mar. 1985.
Raj, Sandeep et al, "A knowledge-based real time embedded platform for arrhythmia beat classification", Biomedicine Eng. Letters, vol. 5, pp. 271-280, 2015.
Madani, Ali et al "Fast and accurate view classification of echocardiograms using deep learning", Digital Medicine, Nature, Digital Medicine, 2017.
Tiwari, Abhishek et al "Mitral Valve Annulus Localization in 3D Echocardiography", IEEE 2016, pp. 1087-1090.
Mansi, Tommaso et al "An Integrated Framework for Finite-Element Modeling of Mitral Valve Biomechanics from Medical Images: Application to MitralClip Intervention Planning", Medical Image Analysis, 2012.
Wang, Yang et al "Automatic Detection and Quantification of Mitral Regurgitation on TTE with Application to Assist Mitral Clip Planning and Evaluation", Image and Computer Vision, Jan. 2013.
He, Kaiming et al "Deep Residual Learning for Image Recognition", 2015.

* cited by examiner

SIGNAL-TRIGGERED INTERVENTIONAL DEVICE CONTROL

CROSS-REFERENCE TO PRIOR APPLICATIONS

This application is the U.S. National Phase application under 35 U.S.C. § 371 of International Application No. PCT/EP2020/071211, filed on Jul. 28, 2020, which claims the benefit of European Patent Application No. 19188989.8, filed on Jul. 30, 2019. These applications are hereby incorporated by reference herein.

FIELD OF THE INVENTION

The invention relates to a system for supporting a medical procedure, to a medical arrangement, to a deployment device, to a computer implemented method for supporting a medical procedure, to a method of training a machine learning component, to a computer program element, and to a computer readable medium.

BACKGROUND OF THE INVENTION

Heart disease is still one of the leading causes of death in the world.

Elaborate schemes have been devised to maintain or restore heart function. One point of failure in the human heart are the heart valves, such as mitral valve regurgitation. Some of these schemes include image/based minimal invasive interventions. Under image guidance, a medical device, such as mitral valve clip is introduced into the heart. The clip is deployed in the beating heart to reduce or even eliminate entirely regurgitation. Deploying the clip correctly is a demanding task, calling for great skills on the part of the operator. The task can be quite lengthy: it often takes various attempts for the operator to correctly place the clip. There are other tasks than Mitral Valve clipping where operators face similar challenges, such as in minimal invasive heart valve replacement.

Health systems around the world are under increasing pressure caused by the "double whammy" of budget cuts and ever increasing demand for such services from an aging population.

SUMMARY OF THE INVENTION

There may therefore be a need for methods and systems that assist medical staff in performing medical procedures more efficiently.

The object of the present invention is solved by the subject matter of the independent claims where further embodiments are incorporated in the dependent claims. It should be noted that the following described aspect of the invention equally applies to the medical arrangement, to the deployment device, to the computer implemented method for supporting a medical procedure, to the method of training a machine learning component, to the computer program element, and to the computer readable medium.

According to a first aspect of the invention there is provided a system for supporting a medical procedure, comprising:

an interface for receiving at least one medical input signal that describes a state of a target anatomy; and
a signal analyzer configured to analyze the medical input signal to determine a time window for deployment of a cardiovascular device to be deployed by a deployment device in relation to the target anatomy.

In particular, the medical input signal includes i) a medical image of the target anatomy acquired by an imaging apparatus and ii) a physiological signal of the target anatomy acquired by a measuring device, and the signal analyzer is configured to analyze both the medical image and the physiological signal.

The cardiovascular device may include a mitral valve clip or a heart valve or any other part that can be deployed in a human or mammal heart.

The "deployment window" as used herein may indicate a true time period for deployment, with a beginning and a (non-zero) length. However, "degenerated" time windows of length zero, that is, time instants, are also envisaged herein.

In embodiments, the deployment device is capable of transitioning between at least two states, including a release state in which the cardiovascular device is deployable, and a retain state, in which the cardiovascular device is not deployable (so is retained), wherein the transitioning is in response to a control signal.

In automatic embodiments, there is computer implemented controller unit that is configured to issue, based on the determined time window, the or a control signal to affect operation of the deployment device.

In embodiments, the system further comprises an output interface with a transducer configured to provide a sensory indication on whether or not the deployment window or instant has been so determined. The sensory indication may be used to indicate to a user when to operate a manual interface of the deployment device to issue a manual control signal to request the transitioning.

The sensory indication may be output through an output. The sensory indication may include an acoustic alert signal (a "beep"), haptic feedback, e.g. by having a handle of the deployment device vibrate to indicate a pending deployment window, or an optical indication, e.g. a (dedicated) flash lamp on the deployment device or elsewhere, or a graphical widget displayed on a display device, e.g., on a monitor etc.

The controller may also be used in embodiments that include user intervention. Specifically, in embodiments, the deployment device includes a manual interface operable by a user to issue a manual control signal in an attempt to effect the transitioning, wherein the control signal issued by the controller blocks at least temporarily, or delays, the manual control signal, if the manual control signal is received outside the deployment window. Specifically, the manual control signal may be delayed until a new deployment window has been found. In other words, there are, in embodiments, two signals involved: one, the manual control signal, caused by the user to request the device be deployed and the control signal issued by the control device in relation to whether a deployment window/instant has been found. In other words, the control signal by the controller can effectively "override" the manual control signal to ensure the cardiovascular (or other payload) device is deployed only during an (allowable) deployment window. In embodiments, the user may request a transitioning back from release state to retain state, if the user feels the deployment is not optimal, although it is expected that this circumstance arises only exceptionally.

In a preferred embodiment both signals are used in the analysis, in order to ascertain not only the state of the organ but also a geometrical/mechanical relationship between the cardiovascular device and the target anatomy. This allows an accurate and robust determination of the deployment window and increases the chances that a successful deployment may be achieved at a first attempt thus making the procedure more time efficient.

In embodiments, the medical image is any one or more of a MRI, X-ray or ultrasound image, and/or wherein the physiological signal is an ECG signal or a breathing signal or other suitable vital sign signal.

In embodiments, the target anatomy is a part of a human or animal vasculature or is a part of a human or animal heart.

In embodiments, the cardiovascular or other payload device includes any one or more of: i) a mitral clip, ii) a replacement heart valve, and/or wherein the deployment device includes a catheter and/or a robotic device.

In embodiments, the signal analyzer includes a pre-trained machine learning component. The machine learning component may be arranged as neural network model, with its parameters adapted in previous learning scheme, such as forward-backward propagation or other gradient-based techniques.

In embodiments, the machine learning component is based on any one or more of: a neural network, a support vector machine, a decision tree. A convolutional neural network in deep architecture is envisaged in embodiment. A plain or residual architecture may be used.

According to another aspect there is provided an arrangement comprising: the system as per any one of the previous embodiments, and at least one apparatus to measure the medical input signal.

In embodiments, the arrangement further comprises the deployment device. The deployment device may include a catheter device configured to deliver to the cardiovascular device.

According to another aspect there is provided a deployment device for deploying a cardiovascular device (or other payload device) at a target anatomy, the deployment device capable of transitioning between at least two states, including a release state in which the payload device is deployable, and a retain state, in which the payload device is retained, that is, is not deployable, the deployment device including an interface configured to enable or disable (e.g., block or delay) the transitioning in response to a control signal as issued by embodiments of a system as herein disclosed.

The proposed system can help a medical user to quickly achieve correct deployment. Specifically, the number of attempts to achieve a proper deployment can be reduced, with proper deployment achievable first time around. In mitral clip delivery, the likelihood of a good clinical outcome, that is, a reduction or even complete elimination of regurgitation can be improved.

In embodiments, the medical signal includes ECG measurements. This is analyzed to detect a desired heart phase, such induced asystole, to prevent attempted deployment of the medical device in the wrong heart phase. A manual/automatic deployment is only allowed by the system in the right heart phase.

In addition, image recognition techniques, e.g. machine learning techniques trained with neural networks on reference images representing good instances for deployment, are used to analyze medical image data thereby recognizing when the device can be properly deployed. In certain examples, the signal analyzer is configured to analyze medical image data so as to find an instance of a desired geometrical or mechano-geometrical configuration between the cardiovascular device to be deployed, such as a mitral clip, and the target anatomy.

In certain embodiments, a combined time window is determined based on the heart phase analysis and the image analysis providing a best opportunity for cardiovascular device deployment.

The proposed system allows to interfere with the delivery system whilst the user attempts manually controlling the delivery device to effect deployment (e.g. closing a mitral valve clip). The system may stop deployment, based on analysis of the medical signal or may re-allow deployment to continue, based on the analysis.

According to another aspect there is provided a computer-implemented method for supporting a medical procedure, comprising:

receiving at least one medical input signal that describes a state of a target anatomy, the medical input signal including i) a medical image of the target anatomy acquired by an imaging apparatus, and ii) a physiological signal of the target anatomy acquired by a measuring device; and analyzing the medical input signal to determine a time window for deployment of a cardiovascular device to be deployed by a deployment device in relation to the target anatomy.

According to another aspect there is provided a method of training a machine learning component as used in the above mentioned embodiments of the system.

According to another aspect there is provided a computer program element, which, when being executed by at least one processing unit, is adapted to cause the processing unit to perform any one of the methods.

According to another aspect there is provided a computer readable medium having stored thereon the program element.

The proposed system is envisaged in embodiments for mitral valve clip delivery, but other minimally invasive heart interventions are also envisaged, such as deployment of replacement valves for the mitral valve or for other valves are also envisaged, and so are other interventions at or around the heart, and indeed interventions in relation to organs other than the heart.

"User" a referred to herein is operator who operates who performs an intervention, in particular who operates the deployment device.

"Patient" is a person or an animal (in particular a mammal) who is the subject of the intervention.

"Machine learning ("ML") component" is any computing unit or arrangement that implements a ML algorithm. An ML algorithm is capable of learning from examples ("training data"). The learning, that is, the performance by the ML component of a task measurable by a performance metric, generally improves with the training data. Some ML algorithms are based on an ML model that is adapted based on the training data. In particular, parameter of the model may be so adapted.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
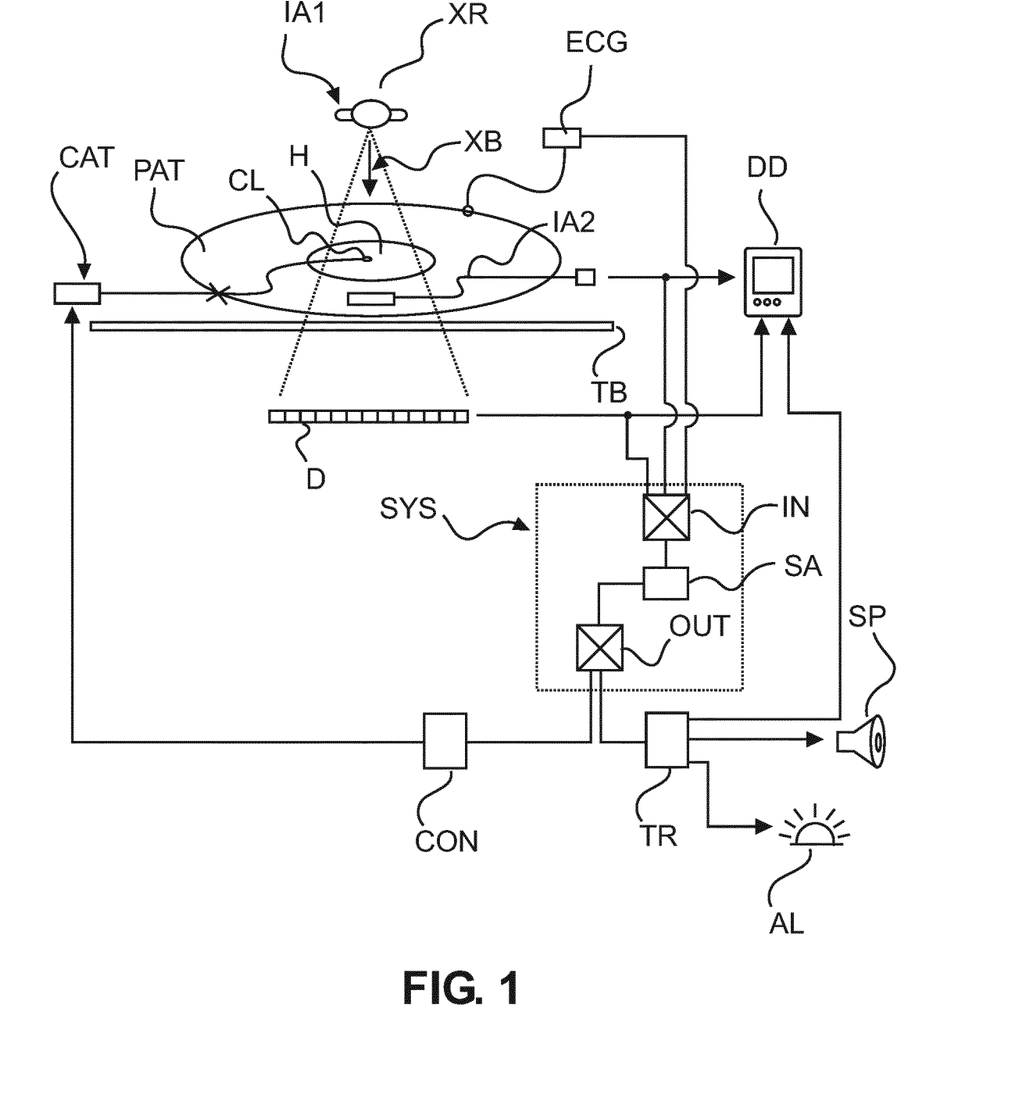
FIG. 1 shows a computerized imaging arrangement for supporting a medical procedure.

FIG. 1 shows a system for image-based support of a medical intervention.

The system may include one or more imaging modalities IA1, IA2, for example an ultra-sound system IA2 having an ultrasound probe TR capable of acquiring a series of images within a patient PAT. US (ultrasound) is merely an exemplary embodiment and other image modalities are also envisaged. Imagery produced by the imaging modality US IA2 can be rendered for view on a display device (e.g., a monitor) DD to support the intervention.

The system may provide image-based support when using a medical tool CAT for performing an action at a lesioned site in or at an OOI (organ of interest) inside the body of patient PAT. In embodiments, the OOI is a human or mammal heart H. The tool CAT may include a catheter, a guide wire, grabbers, etc., depending on the task at hand.

Optionally, a further image channel may be used, such as provided by a fluoroscopic live image stream supplied by an X-ray imaging apparatus IA1 having an X-ray source XR and an X-ray detector D. Patient PAT is preferably arranged on a table TB or other support, with at least a part of the patient PAT situated between X-ray source XR and X-ray detector. In use, The X-ray source is energized to produce an X-ray beam XB that traverses the patient at the OOI and is then registered at the detector as intensities. Acquisition circuitry converts the intensities into an image, or an image stream, that is displayed on the display device DD or on a different display device. Imaging modalities other than MRI or PET/SPECT or yet others are also envisaged herein. The X-ray imaging apparatus IA1 may be used in combination with US modality IA2, or instead of the US (or other) imaging modality IA2.

Briefly, the proposed image processing system SYS operates on a multi-channel medical signal stream. The signals are analyzed by a signal analyzer SA to compute a time window when best to deploy a medical device MC at the lesion. The system SYS may be operable in either of two modes or the two modes may be combined. In one mode, the time window may include a start time and a non-zero length to so define a true time period. Alternatively, to support real-time analysis, the time window may be "degenerate" with length zero, to so define a time instant. The earlier mode may be referred to herein as "predictor mode" as the system predicts the window to extend at the said time length into the future, whilst the latter mode may be referred to herein as the "real-time" mode, in which the system computes whether for a given time instant deployment is advised or not. The, preferably, real-time computation of the deployment instant may be in real-time with respect to the frame or sample rate at which data is supplied in the one or two channels. In real-time mode, the degenerated time window for deployment (also referred to herein as the "deployment instant") may be recomputed for each new data in the channels, although this may not necessarily be so in all embodiments, as gaps may be allowed at times, as required.

In one channel, the "physiological channel", measurement in respect of a physiological state of the organ of interest are provided, whilst the other channel, "the image channel", provides information of the mutual geometro-mechanical configuration of the medical device and the organ of interest. Information from both channels are combined to establish the deployment window for deploying the device MC. As will be explained in more detail below, in embodiments, the time window is established if two conditions are met, one in each channel. In particular, the deployment window is established if and only if i) the organ of interest is in a pre-defined physiological state as per measurements in the physiological channel and ii) if there is a pre-defined geometrical relationship between the device and the OOI as per measurements in the image channel. More relaxed embodiments are also envisaged in which only one of the two (or more) channels is considered, at least at times, or at least in which not all channels are considered at all times.

In embodiments, the system comprises an ECG device that provides the physiological channel for the medical signal to be analyzed by the signal analyzer SA. The ECG device includes a set of probes (not shown) attachable to the patient's chest. The probes are coupled through leads to a measurement device. The probes pick up electrical signals on the patient's skin caused by the cardiac activity. The electrical signals are forwarded to the ECG measurement device that processes these signals by conditioning, digitization or otherwise, and produces a stream, that is, a time series of electrical voltage measurements. Patterns of the measured voltage values in this signal can be associated with different heart phases, in particular with the diastolic and the systolic phase, or with any other phase that may be of interest. In embodiments, the systolic phase is of interest as will be explained in more detail below at FIGS. 3,4 but in other contexts, attention to other phases may be called for.

In embodiments, the other channel, the image channel, of the medical multi-channel signal stream is provided by the imagery acquired by the US imager IA2. In embodiments, a TEE modality is used. In particular, the deployment of the device MC, or attempt to deploy, is carried out during constant cine image support from, in embodiments, the TEE. The TEE-US system IA2 includes a flexible probe that is introduced into the patient's mouth about half-way down through the esophagus to thereby position the probe's tip behind the heart (when viewing the patient's PAT chest from front). Once the probe is so positioned, relatively detailed images of the heart anatomy can be acquired. In embodiments, the ultra-sound system IA2 is capable of producing 3D imagery. At the probe's tip a matrix array of a large number of sound pulse transducers is located that together act to produce, at a given frame rate, three dimensional image volumes of the heart in high quality and good resolution. The TEE imagery is displayed during the intervention in a live stream on display device DD.

As mentioned earlier, the modes of operation of the proposed system SYS may be combined. In particular, the system SYS may operate in real-time mode on one channel and/or may operate in predictor mode in the other. In particular, processing of data in the image channel may be done in real-time mode whilst processing of data in the physiological channel may be done in predictor mode, or vice versa.

For illustrative purposes, that are not to be understood as limiting, operation of the system SYS will be explained with reference to an exemplary use case, namely minimal invasive heart intervention, more particularly mitral valve repair in the patient's heart H.

To better explain the operation of the image processing system SYS in more detail, it will be beneficial to briefly outline first some context around mitral valve repair, in particular the underlying anatomy and some basic steps involved in mitral valve repair, with the understanding that this is strictly exemplary only and purely for illustration purposes and in no way limiting. The processor may be used with benefit for other OOIs, not necessarily for heart interventions, but in relations to other organs as well as required.

Figure 2A:
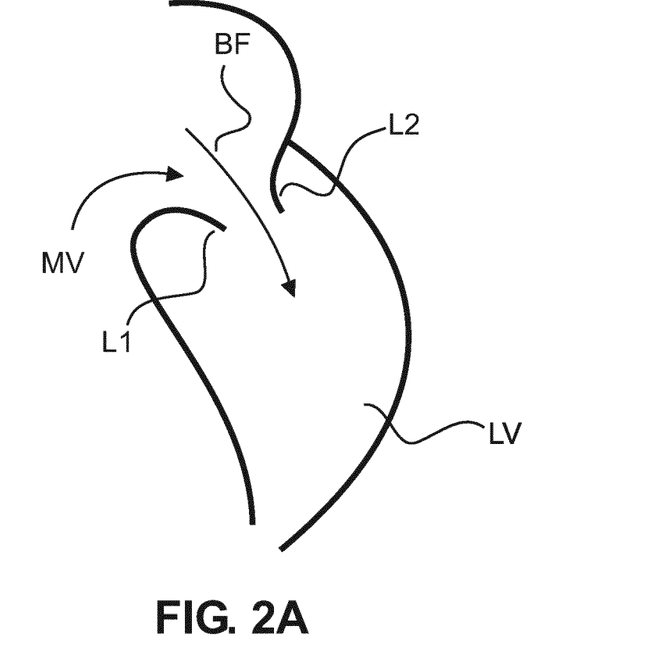
FIG. 2 shows schematic partial cross sections through a human or mammal heart to illustrate cardiac phases.
Figure 2B:
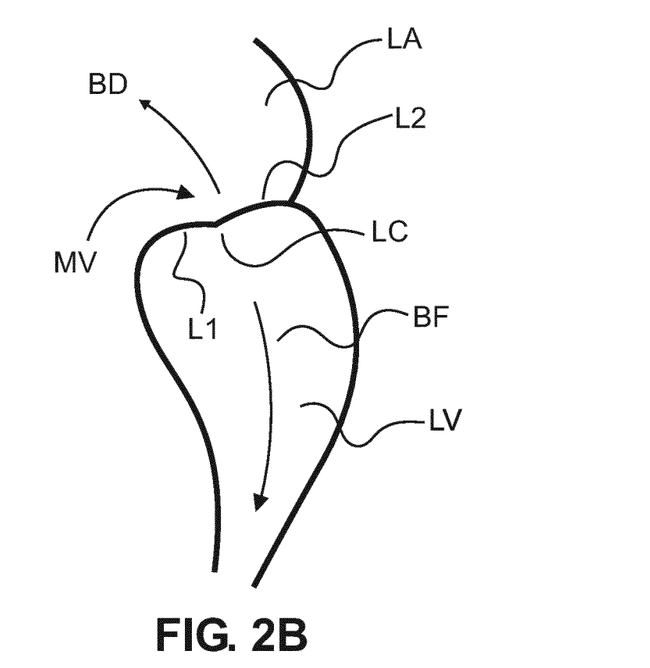

First a few words on the relevant internal heart anatomy with reference to FIGS. 2A,2B. In a preferred embodiment, the OOI includes the mitral valve. This particular heart valve (there are three others) connects the left ventricle LV and left atrium LA in the human or, more generally, the mammal heart H. The mitral valve MV comprises an outer, ring-shaped base (called the (mitral) annulus) that supports a pair of mitral valve leaflets L1,L2. The annulus of the mitral valves changes in shape with leaflet L1,L2 movement in concert with the heart phases, diastole and systole.

The annulus is a flexible deformable structure that contracts and reduces its surface area during ventricular systole to promote complete closure of the leaflets as shown in FIG. 2B. In diastole, the leaflets L1,L2 move forward into the LV for the valve MV to open and to admit blood flow from LA to LV as shown in FIG. 2A.

Figure 3A:
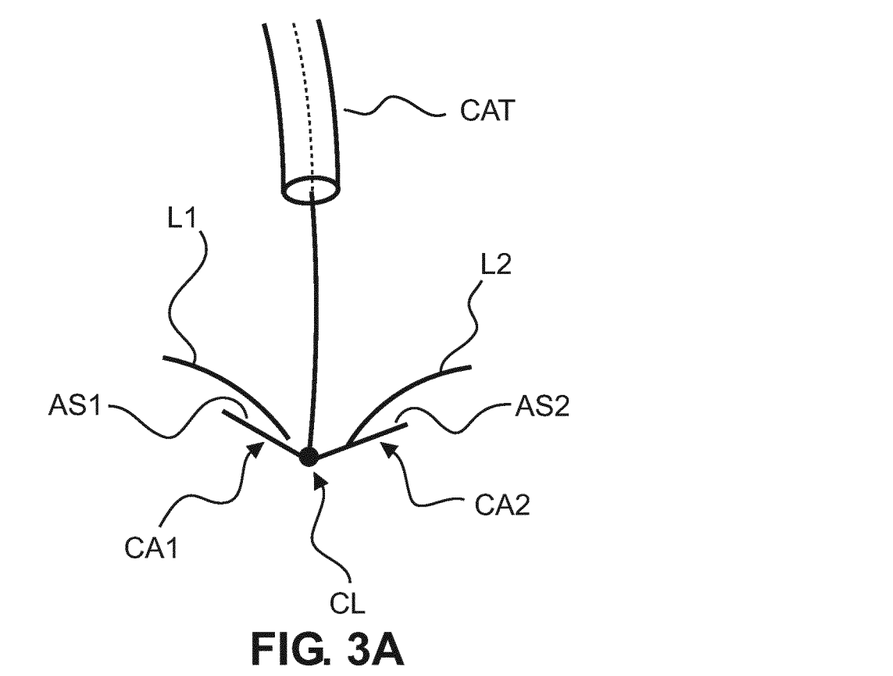
FIG. 3 shows two phases of a medical device to be deployed in a human or mammal heart.
Figure 3B:
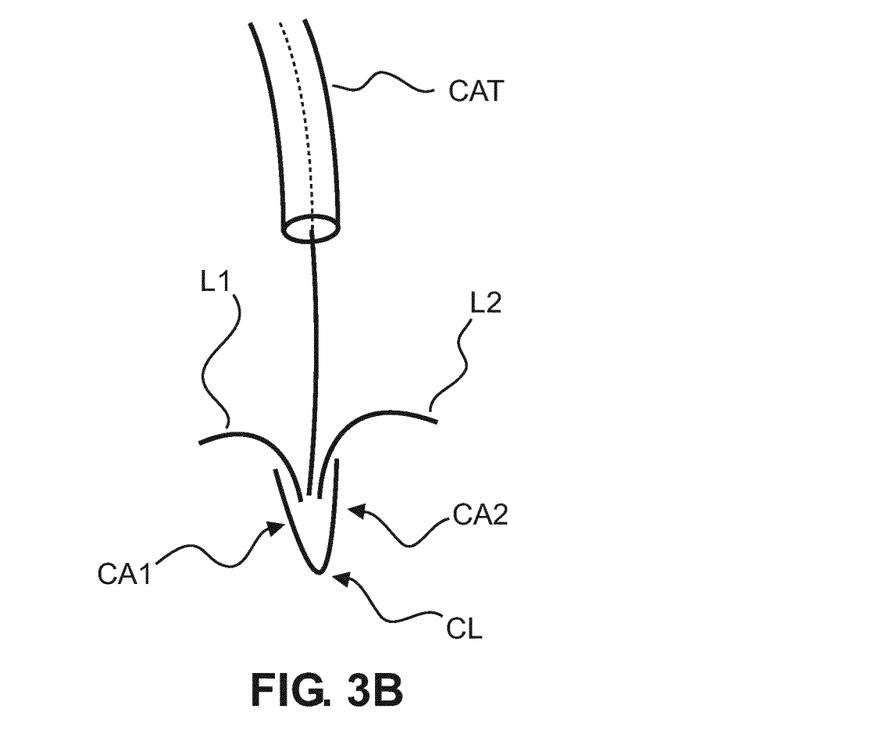

The objective in mitral valve repair is to combat or remedy a heart defect known as mitral regurgitation MR. Essentially, in MR, the mitral valve "leaks". That is, its two leaflets do not completely "co-apt" or meet at the line of coaptation LC when the left ventricle is pressurized (that is during ventricular systole). In other words, as illustrated in FIG. 3B), there remains, at least locally, a "gap" between the two leaflets and blood flows back, it regurgitates, in a backdraught BD, from the LV into the LA. This regurgitation, if left untreated, can cause health problems.

In one technique of mitral valve repair, a specially designed clip is applied at the locale where this gap exists, thereby locally "pinching" together the two leaflets L1,L2 and to thus reduce or even prevent regurgitation. This is illustrated in FIGS. 3A,3B. To achieve this, one may use a delivery system comprising the catheter CAT and a special mitral clip MC positioned at the tip of said catheter. The delivery system may also comprise a steerable guide catheter. The catheter components form a remote controllable (via mechanical levers) system to position and deploy the clip at the mitral valve.

Now, in one variant of the minimal invasive mitral valve repair procedure, the catheter (with the clip MC attached to its tip) is introduced into the patient PAT at an access point (designated as 'x' in FIG. 1), e.g. at the groin and into the femoral vein. The catheter CAT is then advanced all the way up to the vena cava. After a puncturing procedure, the catheter is introduced into the LA and positioned above the mitral valve leaves (FIG. 3A). The catheter is then carefully advanced across the leaflets into the LV, and is rotated so that the plane of the arms perpendicular to the line of coaptation LC. The clip has grabber arms CA1,CA2 with respective grab engagement surfaces AS1,AS2. The grabber arms CA1,CA2 are actuatable by a user through a delivery system including a catheter CAT, to be discussed more fully below. Alternatively, the clip may be actuatable by a fully or partly autonomous robotic control systems. The arms may be caused by the user or robot through the delivery system to move around a pivot PP, with arms movable away from each other or towards each other, forming an angle, for example, between 0° and 180 or even up to 240°. The user may control the clip arm motion from the other end of the catheter CAT. At a suitable moment, which the system SYS helps to establish (to be explained more fully below), the catheter tip is then quickly retracted from the LV back into the direction of the LA whilst the clip is then operated to grab and then pinch together (FIG. 3B) the two leaflets where the gap would form. The clip is then disengaged from the catheter and left in-situ. The catheter CAT is then removed which concludes the intervention.

Application of the clip MC in this manner is no mean feat. It may be worthwhile recalling that the clip is applied during regular heart operation. In particular, the grab-and-clip action is done whilst the leaflets are oscillating and the mitral annulus is moving up and down with the heart action or due to breathing motion. On the part of the tool operator and/or the supporting (inter-disciplinary) team, this requires high concentration, very good eye-hand coordination and a great deal of experience in (spatially) interpreting the supporting imagery produced by the imaging modality.

Figure 4:
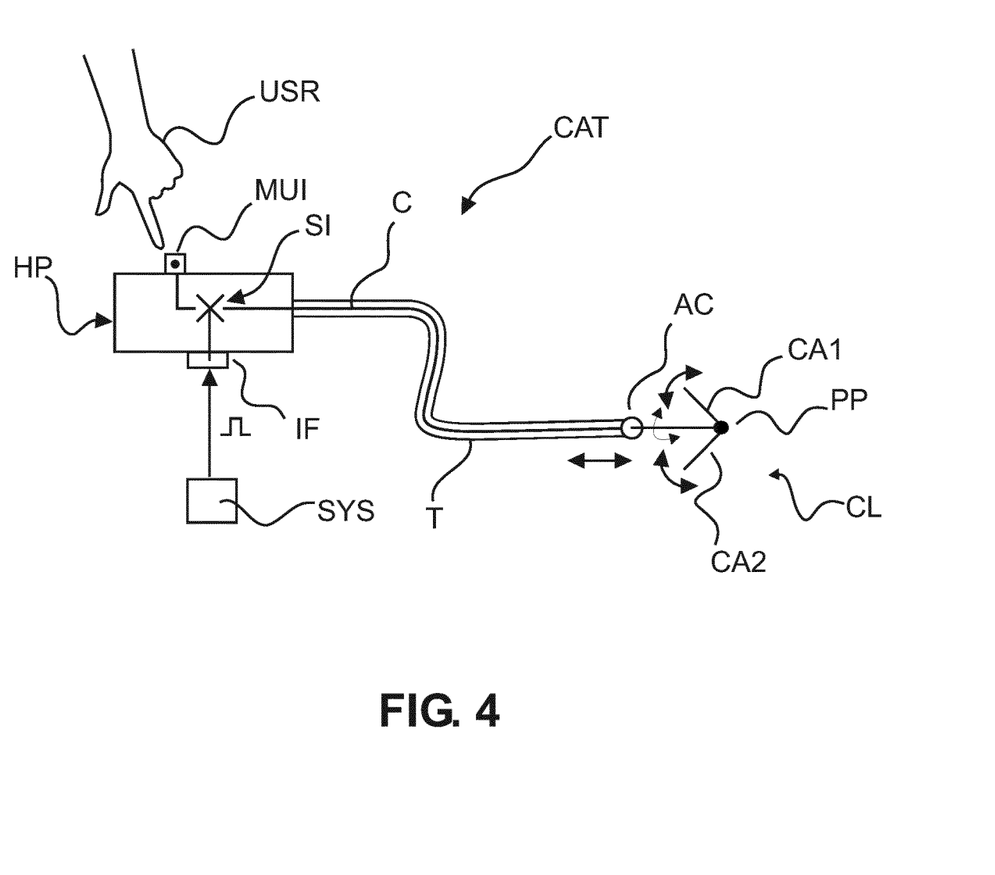
FIG. 4 shows a delivery system to deliver a medical device in an intervention.

Reference is now made to FIG. 4 which shows a schematic block diagram of the clip delivery system including the clip MC attached to a tip portion of a catheter device CAT. The catheter device includes broadly a hand-piece HP at a proximal end (the user end) of a flexible tube T that terminates at its other, the proximal end or tip portion, at an actuator AC to which the clip is removably attached.

The flexible tube T of the catheter CAT incorporates a coupling system S that couples a manual user interface MUI to the actuator AC, and hence to the clip MC. The coupling is mechanical, electrical or mechano-electrical, or a combination thereof. User interface MUI may include a knob, lever, button or other, preferably integrated into the hand-piece HP.

The tube tip is bendable and can flex in a number of different spatial directions. The actuator may also be rotatable along the longitudinal axis of the tube. In other words, the clip CL when attached to the tube tip, can be moved in any desired spatial direction in 3D space to be accurately positioned opposite the line of coaptation as explained above in relation to FIG. 2B. Movement of the tube tip, and hence of the clip, is response to the user interface MUI.

The proposed image support system SYS is communicatively coupled to the catheter delivery system CAT through a control signal interface IF. The control signal interface IF is coupled to a signal inhibitor SI. The signal inhibitor SI is operable, based on the control signal from a controller CON of the system SYS, to interrupt or re-establish the signal path between the manual user interface MUI and the clip actuator AC. In other words, the signal inhibiter SI can enable or disable deployment of the clip CL.

As envisaged herein, the interventional support system SYS is a computer implemented. It computes, based on the above described multi-channel medical signal stream, a correct deployment window during which the clip CL should be deployed.

Once system SYS establishes an instance of a deployment window, the signal inhibitor SI is instructed by the system SYS to enable signal path between manual user interface MUI and the AC actuator to deploy clip CL. In other words, within the deployment window the user USR can operate the manual user interface MUI to effect the deployment of the clip at his or her leisure. However, outside the deployment window the signal inhibitor SI cuts the signal path so that the user can no longer effect the deployment of the clip, even when operating the manual user interface. In one embodiment, if this happens, that is, if the user requests deployment and this is blocked because deployment is requested outside the deployment window, this request is stored in a buffer (not shown). Once the next deployment window is detected, the signal inhibitor enables or re-enables the signal path and the buffered signal is forwarded to the actuator to effect deployment of the clip. The user may thus experience this as a delayed deployment. In a fully automatic embodiment, where the delivery system is robotic system, the system controls deployment directly. That is, once system establishes the deployment window, a control signal to deploy is sent through the signal interface to the actuator to effect clip deployment.

Referring now in more detail to the clip MC, this includes the two opposed arms CA1, CA2. The two arms CA1, CA2 are joined, at one of their ends, at a pivot point PP. The two arms are pivotable about the (common) pivot point PP upon operation of the actuator AC. The catheter or the actuator is operable, upon user request through MUI, so that the clip can be transitioned between two phases either way, between an open phase and a closed phase. In the closed phase, the grabber arms CA1 and CA2 are drawn towards each other to effect the pinching action on the leaflets, thereby forcing parts of the leaflets towards each other. In the closed state, during deployment, the angle between the two arms is substantially 0°. However, the pinching may also be reversible, so long as the clip is not detached ("full deployment"). That is, the clip may be re-opened by the actuator, thereby moving the free ends of the arms away from each other to form an angle other than 0°, such as up to 240°, 180°, or as required by the user. The user can first request through the manual user interface to open and then close the clip, the clip thereby transitioning between an open and closed state. For full deployment, once the user is satisfied that the clip has been properly deployed, the catheter tip T can be detached from the clip by operation of the (or other) user interface MUI, thus leaving the clip in situ at the valve. The catheter can then be withdrawn from within the patient thereby concluding the intervention.

Corresponding to the state of the clip, the actuator of the delivery device CAT may accordingly transition between two states, a retain state and a deployment state. In deployment state, the actuator causes the arms to close, whilst in retain state, the arms of the clip are caused to open.

Although not shown in FIG. 4, the delivery system CAT may also include additional clip grippers that drop during deployment into the clip arms to essentially push the leaflets on the respective engagement surfaces AS, AS2 of the respective clip arms CA1, CA2.

The signal inhibitor SI may be implemented purely by electrical means to simply interrupt signal flow from the user interface MUI to the actuator AC. The signal inhibitor may thus be arranged as a simple switch. Alternatively, or in addition, mechanical or mechano-electrical embodiments are also envisaged where the signal inhibitor is arranged as a pivotable pin that releasably engages a ratchet system connected to the MUI, thereby preventing the user to operate for instance a rotatable knob which may form part of the mechanical user interface.

Explaining now in more detail operation of the computerized system SYS, this may be arranged in hardware or software or in a combination of both. The medical support system may be implemented on a single computing device resident in the operating theatre such as in a computing unit communicatively coupled to the delivery system CAT and/or the monitor DD. The computing system may be workstation or operator console associated with one of the imaging modalities IA1, IA2. Alternatively, the system SYS is remotely arranged and coupled through a suitable communication network with the catheter CAT. In other embodiments, the system is fully integrated into the catheter system with interfaces IN arranged to receive the one or more medical signals.

Preferably, as mentioned, the two medical signals, the ECG signal stream and the image stream, are processed in combination in a logical AND operation. Alternatively, only a single stream may be processed so that the processing of the system is based solely on the ECG signal for instance or solely on the image stream. The imagery may be provided by any suitable imaging modality, such as ultrasound (e.g., TEE), x-ray (CT or radiography), MM or any other, as called for by the medical task at hand. The physiological signals are preferably provided by an ECG apparatus, but in alternative embodiments, for other interventions, a instrumentation other than ECG may be more apt that measures a different quantity of interest.

With continued reference to FIG. 1, the computerized system SYS includes a signal interface IN through which the medical signal(s) in the one or two channels is received. The signals are then analyzed by the signal analyzer SA to compute the deployment window. The signal analyzer SA may be coupled to the controller CON. The signal analyzer provides through an output interface OUT to the controller CON an indication once a deployment window is found. The controller then converts this indication (a number, flag, code or other) into the control signal to control the catheter delivery system CAT as described above in FIGS. 3-5.

In particular, the control signal may disable or enable the manual user interface MUI through the signal inhibitor SI as described above. Alternatively, or in addition, in fully autonomous robotic environment the control signal provides through suitable interfaces a control signal to the robotic device to automatically and directly affect the deployment once the deployment window has been found by the signal analyzer SA.

In addition, or instead of facilitating user operation through user interface MIU or fully automatic deployment control in a robotic system, the output signaling provided through output interface OUT may include a transducer TR. The output signaling may be processed by the transducer TR to provide a sensory indication to the user in relation to the deployment window. The user is informed whether or not a deployment window has been established. The sensory indication may be in the form of sound by sounding out an alert signal through the speaker SP or optical signaling, such as by activating/deactivating an alert lamp AL. In addition, or instead, the transducer TR may include, or may be coupled to, a visualizer module capable of generating a suitable graphical indication that is displayed in a graphics display on the display device DD, along, or instead of, current imagery as supplied by the TEE IA2 or X-ray system IA1 or whatever the modality used. The graphical indication may be display on a different display device than the display device used of the imagery. The graphical indication may include one or more bar or line segments to indicate the deployment window in predictor mode or the graphical indication may include symbology to indicate in real-time mode that deployment is or is not advised/allowed.

In embodiments, no such sensory indication is provided if no deployment window is found, with an indication only provided once a deployment window has been found. Alternatively, or in addition, the fact that no deployment device is found is also indicated by a certain sound, a certain color or frequency of the alert flash-light and/or by an indication on the display device to hold deployment. Once the deployment window is found, this indication changes into a "go-ahead signal" by displaying a suitable symbol on the display device DD, or by changing the sound as sounded out through the speaker or by changing the frequency or color of the indicator light AL, etc.

Explained now in more detail operation of the signal analyzer SA in predictor mode, the analysis of the signal representative of the physiological state, for instance the heart phase, may be based on finding signal pattern. For instance, the electrocardiogram is a voltage versus time curve. Analyzing this curve for a number of cycles allows establishing the actual heart rate, along with substructures (that is patterns of sub-sections of the curve that represent a heart phase of interest) and the time when each heart beat begins. For instance, the signal analyzer SA may the analyze the received voltage versus time signal for a certain signal pattern such as the QRS complex. In yet more detail, the beginning of a desired heart phase and its duration can be derived using methods for (quasi-real time) detection of the QRS complex. The deployment window may then be extrapolated on the basis of the actual heart rate and the said duration for future heart cycles. More refined embodiments of the signal analyzer SA are also envisaged that further analyze whether heart rate increases or decreases and that then adapt the length and the relevant substructure of a heart cycle accordingly. In this manner, the deployment window, as a true time interval, suitable for device deployment can be provided. In addition or instead, in real-time mode, methods for real-time heartbeat classification may be used to identify arrhythmia or, more generally, situations where device deployment (or device deployment during the next heartbeat) is undesirable.

Figure 5A:
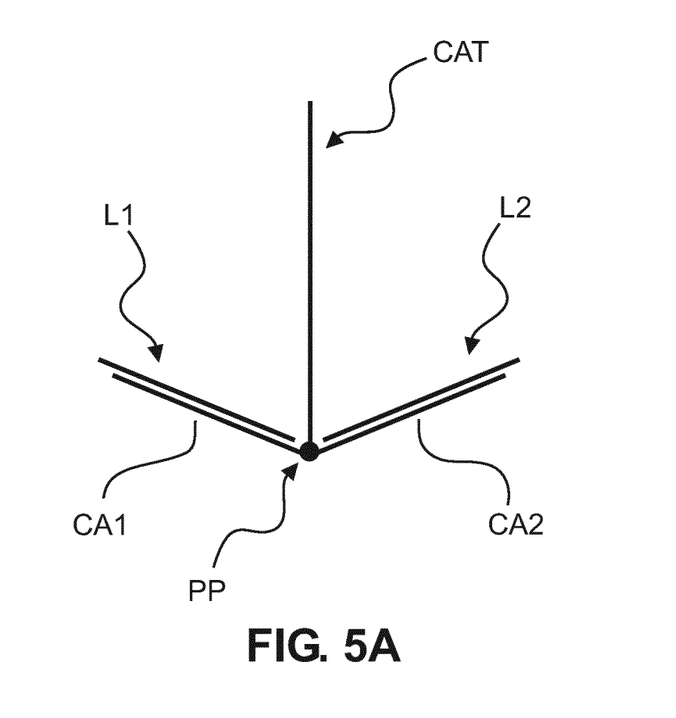
FIG. 5 shows a schematic drawing in side view of two states of a medical device to be deployed.
Figure 5B:
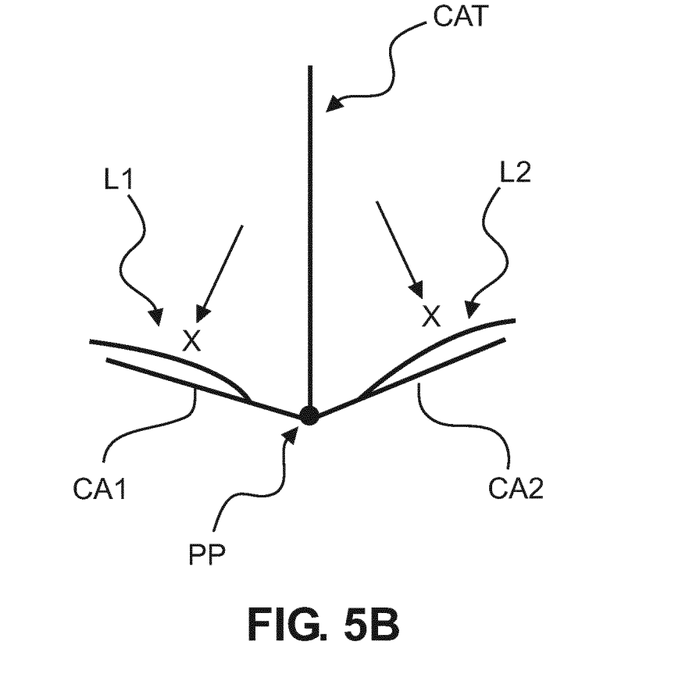

In addition, or instead of the physiological signal, the image stream provided by the US (e.g., TEE) or X-ray, or by any other suitable imaging equipment, is analyzed for patterns that are indicative for a suitable deployment window. This image-based analysis is preferably envisaged for real-time mode and is explained in more detail with reference to FIGS. 5A and 5B. More specifically, FIG. 5A is a schematic representation in sectional view of a geometry that has been found by Applicant to represent an instance of a correct deployment window. The geometry as shown in FIG. 5 as may be present in a currently received frame of the monitored image stream, constitutes an instance of the deployment window because the leaflets L1,L2 lie out flat on the engagement surfaces AS1,AS2 (assuming these are flat) of the two arms CA1,CA2. In general, the shape of the leaflets during contact essentially follow the contours of the engagement surfaces AS1,AS2 of the two arms CA1, CA2. In particular, both leaflet contours L1 and L2 follow the contours of the respective arm's surface AS1, AS2. The geometric situation shown in FIG. 5A is hence referred to herein as the snug fit condition. Geometrically and mechanically, this condition represents contact of at the least the $1^{st}$ order, with parallel tangent planes. In contrast, an instant not suitable for deployment is indicated in FIG. 5B, where the snug fit condition is not fulfilled as the leaflets L1 and L2 have, at locations (indicated in the drawing by 'x'), ripples or folds, that is, locations that do not follow the contours of the surfaces of the arms CA1 and CA2. Such ripples or other contour mismatches may be formed for instance by instantaneously emerging, unfavorably directed blood flow currents or eddies.

Deploying the clip CL in situation 5B may lead to inferior results that may not sufficiently combat or close off the regurgitation. However, in the snug fit condition as shown schematically in FIG. 5A, deployment will result in most cases in a reliable occlusion of the regurgitation locally. Advantageously, in the multi-channel embodiment of the proposed support system SYS, there is no sole reliance on the physiological channel, because even though the heart may be in systolic phase, and thus the mitral valve is open, if there is no snug fit with the grabbers' surfaces, the intervention is unlikely to be successful as residual regurgitation may still remain. Also, it is highly unlikely for the deployment to succeed if one attempts to operate outside the systolic phase. But, as proposed herein in embodiments, by combining information from both channels, the image channel and the physiological channel, the intervention can be shortened by being able to deploy correctly and quickly.

In principle, and as is envisaged in embodiments, the snug fit requirement can be established based on traditional image analysis techniques which include segmenting the said image frames for the leaflets and the arms. Tangent planes, or, depending on the dimensionality of the imagery, tangent lines for the two segmented structures can be established to so assess the level of osculation between the curves or surfaces.

However, instead of using such segmentation-based techniques, other embodiments are envisaged where machine learning techniques are used instead, such as deep learning with neural-networks or other. The assumption in these machine learning approaches is that there is a latent mapping between the imagery and labels, in this case 2, indicating suitable for deployment or not suitable for deployment. This underlying latent mapping is as such not known but can be learned from training data. In particular, training data may be acquired in a supervised learning scheme. A similar analysis based on machine learning models may also be used for analyzing the ECG signals to identify properly the desired phase the systolic or diastolic or other phase of interest. These ML based embodiments will be explained below at FIGS. 8,9 in more detail.

In real time mode, this analysis by analyzer SA is preferably done for each image frame or every n-th frame (n<1) or at random, and for every such instant it is determined whether or not to deploy.

In addition or instead, in predictor mode, the deployment window, a true time period, can be computed, given a certain image and/or ECG reading. In this manner, a true time period rather than a time instant may be indicated to form the deployment window. The prediction may be done by the analyzer SA analyzing initially a plurality of frames and/or ECG readings, over one or more heart cycles, and then predicting the time window. Response of the system may be slower because of this latency.

In more detail, the predictor mode is based on the insight that the received image sequence of the mitral valve provides the times when the mitral valve opens (i.e. beginning of the contraction of the left atrium LA) and the times of when the mitral valve closes (i.e., end of left atrium LA contraction). This information on the valves MV's opening and closing times forms patient characteristic information about the length of the heart cycle (repeated valve opening) and its patient individual signal structure as provided by the tandem physiological signal, e.g. the ECG signal. In other words, the individual heart rate of the given patient can be estimated. If these events, i.e., the valve being open or closed, have been identified over previous frames, the heart rate, and hence the deployment window, can be predicted by extrapolation as mentioned above. In embodiments, state-space models may be used where the states represent the different heart phases. In addition or instead, the extrapolation may be done by a machine learning model pre-trained on training data including such historic image sequences and/or ECG data.

Figure 6:
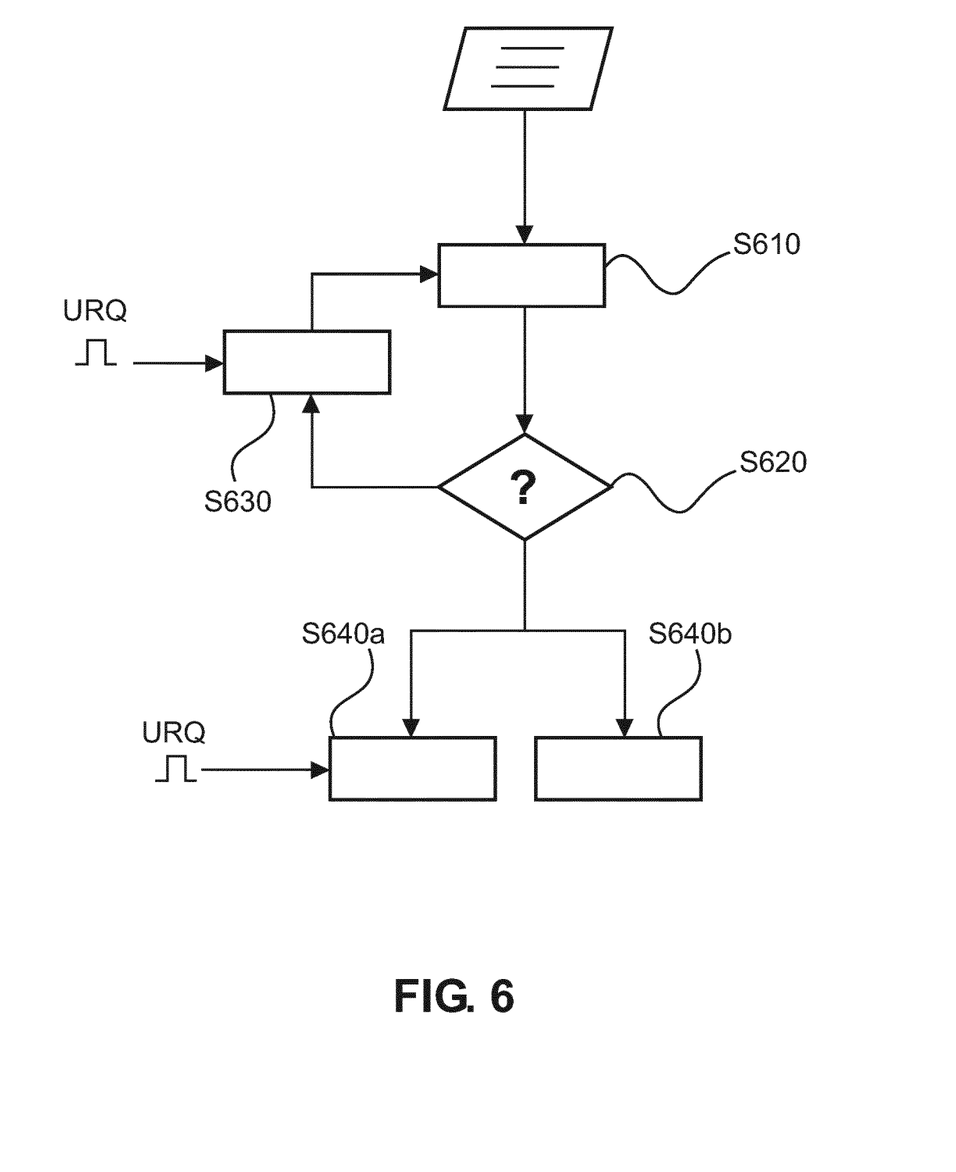
FIG. 6 shows a computer implemented method of supporting a medical procedure.

Reference is now made to FIG. 6 which shows a flow chart of a computerized method of supporting a medical procedure such as the one described above in FIGS. 1-5. However, it will be understood that the following described method steps are not necessarily tied to the architecture of FIGS. 1,4, and the following steps may also be understood as a teaching in its own right.

At step S610, one or more medical signals are received. Medical signals may include an image of the anatomy of interest, and a signal that represents a physiological state of this anatomy. In embodiments, the anatomy includes a mammal (human or animal) heart, in particular valve thereof, such as the mitral valve or other. The medical procedure may be one of minimal invasive valve repair. For example, embodiments include the human heart, in particular imagery that shows parts of the human heart, in particular, a mitral valve or other valve and the other signal is an ECG signal that represents cardiac phases. A phase of interest is the systolic phase, but other cardiac phases such as diastolic or a phase in between the two may be called for in other interventions. In other embodiments, the phases refer to other organs, such as phases of the breathing cycle in lung imaging, or other.

At step S620 the one or more medical signals are analyzed to establish a time window for deployment of a medical device, in particular a cardio-vascular device such as a mitral clip. The medical device is deployed by a deployment device such as a catheter, as described in FIG. 4.

In mitral clip deployment, a clip CL is to be deployed. The clip is attached to leaflets of the mitral valve during an intervention. In a preferred embodiment, information from both signal streams, the physiological stream and the image stream are combined in the analysis. In other embodiments, however, only one stream is considered although this is less preferable. In embodiments the time window for embodiments is established if the heart, as per the physiological ECG signal, is in its desired heart phase. This represents a physiological condition. In addition, the imagery in the image stream is analyzed to find an instance of a desired geometrical or mechano-geometrical configuration between the device to be deployed, for instance the mitral clip, and the target anatomy, in this case the leaflets of the mitral valve. This latter condition may be referred to as the snug fit condition as introduced above at FIG. 5. Preferably, only if both conditions are met, is the conclusion reached that there is an instant of a deployment window to deploy the device.

If it is established at step S620 that, based on the current medical signals, no deployment window can be established, the signal flow returns to step S610 to receive follow-up imagery and the method continues monitoring the incoming signal stream. If, in this situation, a user request is received at step S630 to still deploy, this request is rejected, and deployment is blocked.

However, if it is established at step S620 that there is an instant of a deployment window, an earlier logged request for deployment at S630 is now allowed and deployment may be facilitated or effected at step S640a. Alternatively, if request for deployment is received first time in this window, the deployment is also initiated.

Effecting or facilitating deployment may include providing a visual or other sensory indication to the user that a suitable deployment window has been found.

Alternatively, in a fully automatic autonomous setting, a control signal is sent to a robotic delivery system at step S640b to automatically, without user interaction, effect the deployment.

Deployment may include in either case controlling an actuator of the delivery device in order to transition the clip from an open into a closed position to affect the above described action of pinching together of the two leaflets of the mitral valve.

Figure 7:
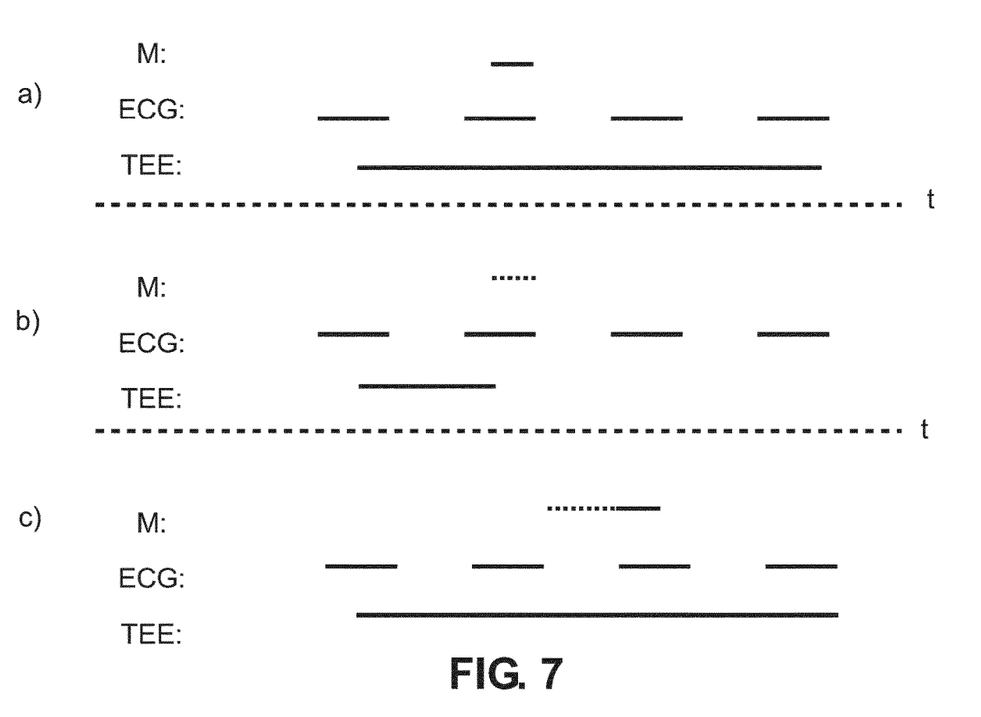
FIG. 7 shows exemplary timing diagrams of deployment windows for a medical device.

Referring now to FIG. 7 this shows three timing diagrams A), B), C) that represent different use cases. The line segments designated as "M" indicate user requests. The line segments in FIG. 7 designated as "ECG" and "TEE" indicate deployment windows over time t per channel. Specifically, line segments "ECG" indicate ECG signals that are indicative for deployment whilst "TEE" segments indicate arrival of imagery that is indicative for deployment. However, in a preferred embodiment, overall deployment window is established only when there is an overlap in time between the per channel windows, that is, if both of the above mentioned conditions are met. The dotted line at "M" indicates blocked user requests for deployment.

The TEE type segments are longer than the respective ECG signals to indicate the different refresh rates with ECG signals reacting much faster than the image refresh rate. More particularly. In diagram, a), user request M is allowed because the per channel windows in channels ECG and TEE overlap. In diagram b), the user request M is rejected. Whilst the analysis of the ECG channel would allow the request, the analysis of the image channel TEE does not. In other words, no deployment window is established. In diagram c), the user request M is initially rejected (as shown in dotted portion) as there is no counterpart window in the ECG channel that could overlap with the image channel window. Later, there is such overlap because a new window in the ECG channel is established with the window in the image channel still pending, so now the deployment request is allowed. In the multi-channel embodiments, there are hence two independent monitoring loops, one for each channel, to establish the respective condition. If both are met, deployment is allowed. The timing diagram in any of FIG. 7 A)-C) with the line or point segments indicative of deployment window or deployment instant respectively, are schematic representations of embodiments envisaged for the above mentioned graphics display.

The above described deployment of a mitral clip is according to one embodiment only, and other applications are also envisaged herein, such as computer-controlled steering of catheters. For example, in case of an aortic stenosis and trans-catheter aortic valve treatment, the catheter needs to be passed through a narrow orifice of calcified aortic valve. When the ventricle is contracting, the blood is pumped through the aortic valve and a blood flow jet pushes the catheter tip away from the orifice making it very difficult to pass the valve in this heart phase. In this embodiment, the ECG signal can be used to prevent pushing the catheter forward when the ventricle is contracting and to select the proper heart phase for passing the aortic valve. The catheter steering through the orifice can be supported only by the physiological channel or instead of, or in addition to, the image channel. In this embodiment, imagery, for example angiographs, is analyzed for the right orifice diameter, for example.

Figure 8:
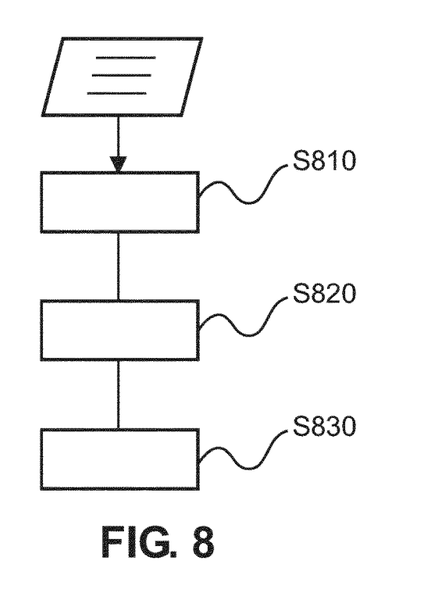
FIG. 8 shows a computer implemented method of training a machine learning model.

Reference is now made to FIG. 8 which shows a flow diagram of a method for training a machine learning model.

The model, once trained, may then be used to implement the above described analysis step S620 or the signal analyzer SA.

More particularly, at step S810, training data is provided preferably as pairs of training input data and their respective target. The training data may be requested from historical data held in medical repositories.

At step S820 a machine learning algorithm is applied to the data to learn the above described latent relationship. This step may include adapting iteratively pre-assigned parameters of the machine learning model. The machine learning model may be implemented as a neural-network, in particular in deep learning architecture.

At step S830, once the model has been sufficiently trained, that is, after a number of iterations that are pre-defined or after fulfilling certain stopping condition, the so trained machine trained learning model can be released for use.

The training data can be retrieved from previously acquired historical imagery and/or electrocardiograms from previous interventions as may be found in hospital PACS systems or other medical data repositories. In particular, medical image datasets representing previous cardiac interventions involving deployment of cardiovascular devices as described herein may be used in model training.

A human expert, such as a radiologist or other (depending on the modality) may review such training imagery to label or annotate same, that is, to indicate, whether or not, the shown instance in the image would be one where deployment is or is not advisable. The expert can thus assign a label, and the training data is then formed by the so labeled training imagery. The labels form the targets for the machine learning model. The model may include a neural-network with two or more hidden layers (deep learning).

The expert may label in addition or instead of the imagery, the historic electrocardiograms. The expert may further indicate as respective targets, estimates for the length of the deployment windows.

Parameters of the model may be adapted in a learning phase based on the training data. In this training phase, parameters initially populated, are adapted in an optimization scheme, such as forward/backward propagation, or other gradient based techniques. The adjustment occurs in one or more iterations that cumulatively of all training data sets arrive at a suitably adjusted neural-network, for instance. Once properly trained, the network can then be used in the signal analyzer. Previously unseen imagery during the use of the system for a given intervention are then fed into the network and are forward propagated to produce a prediction of deployment or not, given the image.

The machine learning model can then analyze new imagery and/or electrocardiograms to predict whether deployment is advisable or not. To ensure quasi real time delivery of deployment window descriptions, it is preferable to train or deploy the machine learning model on a specialized high performance computing unit including data processors configured for parallel computing. Example includes multi-core processors but may also include dedicated specialized chips such as GPU's or others.

Figure 9:
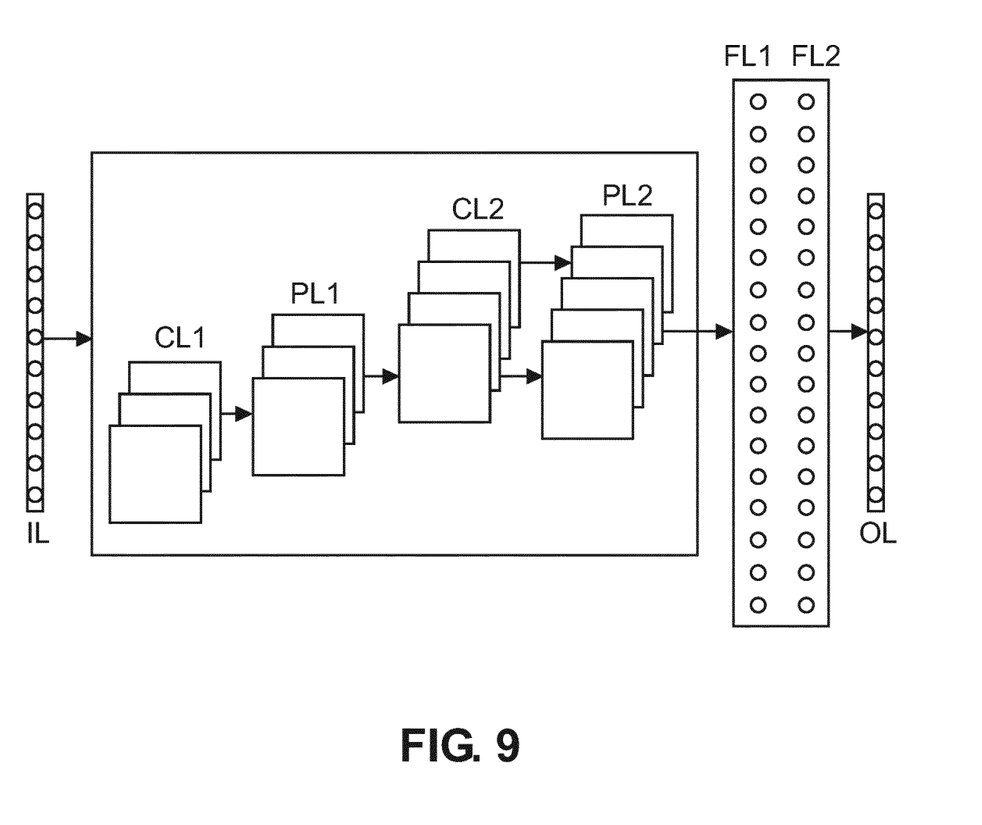
FIG. 9 shows a machine learning model envisaged in embodiments.

Reference is now made to FIG. 9 that shows an example of a machine learning model in terms of deep neural-network including a plurality of hidden layers. More particularly, FIG. 9 is a schematic diagram of a convolutional neural-network CNN envisaged in some, but not necessarily all, embodiments. In particular, this NN embodiment is not at the exclusion of alternative techniques, such as support vector machines, linear or non-linear regression or classification algorithms, decision trees, or otherwise, all equally envisaged herein.

A fully configured NN, as obtained after training (to be described more fully below) may be thought of as a representation of an approximation of the latent mapping between two spaces, i) the space of images and/or ECG readings, and ii) the binary decision space {0,1}, wherein one element represents "deploying" and the other "not deploying". The learning task is hence essentially a classification task where it is to be classified whether a given image does or does not represent an instance of deployment. Alternatively, the latent mapping may be understood as a mapping between i) the space of images and/or ECG readings, and ii) time intervals for predictor mode. The images represent historic samples of the respective intervention one wishes to support, such as (mitral) valve repair by clip deployment or the catheter steering application described above, or any other intervention of interest. A trained machine learning model attempts to approximate this mapping. The approximation may be achieved in a learning or training process where parameters, themselves forming a high dimensional space, are adjusted in an optimization scheme based on training data.

In yet more detail, the machine learning component may be realized as neural-network ("NN"), in particular a convolutional neuro-network ("CNN"). With continued reference to FIG. 11, this shows in more detail a CNN architecture as envisaged herein in embodiments.

The CNN is operable in two modes: "training mode/phase" and "use mode/phase". In training mode, an initial model of the CNN is trained based on a set of training data to produce a trained CNN model. In use mode, the pre-trained CNN model is fed with non-training, new data, to operate during normal use. The training mode may be a one-off operation, or this is continued in repeated training phases to enhance performance. All that has been said so far in relation to the two modes is applicable to any kind of machine learning algorithms and is not restricted to CNNs or, for that matter, NNs.

The CNN comprises a set of interconnected nodes organized in layers. The CNN includes an output layer OL and an input layer IL. The input layer IN is dimensioned to be able to accept the training input image that represents the mutual geometry of the medical device at the organ of interest, such as the mitral clip versus mitral valve. In other words, the input layer IL is a matrix of size m×n, with n,m the number of pixels in m rows and n columns. The output layer OL for the proposed binary classification task can be chosen as a 2D vector (x,y) with one entry, e.g. x, representing "deploying" and the entry, e.g. y, representing "not deploying".

The CNN has preferably a deep learning architecture, that is, in between the OL and IL there is at least one, preferably two or more, hidden layers. Hidden layers may include one or more convolutional layers CL1, CL2 ("CL") and/or one or more pooling layers PL1, PL2 ("PL") and/or one or more fully connected layer FL1, FL2 ("FL"). CLs are not fully connected and/or connections from CL to a next layer may vary but are in generally fixed in FLs. The CNN may be stored in a memory MEM.

Nodes are associated with numbers, called "weights", that represent how the node responds to input from earlier nodes in a preceding layer.

The set of all weights defines a configuration of the CNN. The weights are the parameters of the model. In the learning phase, an initial configuration is adjusted based on the training data using a learning algorithm such as forward-backward ("FB")-propagation or other optimization schemes, such as gradient descent methods or others. Gradients are taken with respect of the parameters of the objective function.

The training mode is preferably supervised, that is, is based on the labeled training data. Labelled training data includes pairs or training data items. For each pair, one item, the image and/or electrocardiogram, is the training input data and the other item, the labeling with '0' or '1', is the target, known a priori to be correctly associated with its training input data item. This association defines the labeling and is preferably provided by a human expert.

In training mode, preferably training input data from multiple such pairs are applied to the input layer to propagate through the CNN until an output emerges at OL. Initially, the output is in general different from the target. During the optimization, the initial configuration is readjusted so as to achieve a good match between input training data and their respective target for all pairs. The match is measured by way of a similarity measure which can be formulated in terms of on objective function, or cost function. The aim is to adjust the parameters to incur low cost, that is, a good match.

More specifically, in the NN model, the input training data items are applied to the input layer (IL) and passed through a cascaded group(s) of convolutional layers CL1, CL2 and possibly one or more pooling layers PL1, PL2, and are finally passed to one or more fully connected layers. The convolutional module is responsible for feature based learning (e.g. identifying features in the patient characteristics and context data, etc.), while the fully connected layers are responsible for more abstract learning, for instance, the impact of the features on the treatment. The output layer OL includes the output data that represents the estimates for the respective targets.

The exact grouping and order of the layers as per FIG. 9 is but one exemplary embodiment, and other groupings and order of layers are also envisaged in different embodiments. Also, the number of layers of each type (that is, any one of CL, FL, PL) may differ from the arrangement shown in FIG. 8. The depth of the CNN may also differ from the one shown in FIG. 9. All that has been said above is of equal application to other NNs envisaged herein, such as fully connected classical perceptron/type NNs, and recurrent NNs, or others. In variance to the above, unsupervised learning or reinforced leaning schemes may also be envisaged in different embodiments. As variance of the NN the "plain" network architecture in FIG. 9, residual network architectures ("ResNet") are also envisaged, where local output from one layer is not feed into the next layer, but one or more such layers are leapfrogged and combined with the output of a down-stream layer. Skipping one or more of such intermediate layers in this manner, allows combating vanishing gradient effects. See for instance Kaiming He et al in "*Deep Residual Learning for Image Recognition*", available online at arXiv: 1512.03385v1 [cs.CV] 10 Dec. 2015.

The labelled training data, as envisaged herein may need to be reformatted into structured form. As mentioned, the labelled training data may be arranged as vectors or matrices or tensors (arrays of dimension higher than 2). This reformatting may be done by a data pre-processor module (not shown), such as scripting program or filter that runs through patient records of a hospital information system or other image repository, to pull up the images for interventions of interest, e.g. mitral valve repair.

The training data sets are applied to an initially configured CNN model and the training data is then processed according to a learning algorithm such as the FB-propagation algorithm as mentioned before. At the end of the training phase, the so pre-trained CNN may then be used to assist the user in interventions to predict the correct deployment window.

The above described ML formalism may also be used to recognize the desired heart phase, and or the ones to avoid, in a given ECG sequence. In this case, the training data pairs comprise instead of or in addition or the imagery, historic ECG curve sections that are labeled by a medical expert with a code for the respective heart phase that the respective section represents. The ECG curve section may be encoded as a vector $(v_1, \ldots v_i, \ldots, v_T)$, with each entry representing a voltage value at time i, whilst the associated label or target is an encoding of the correct heart phase.

Some or all of the above mentioned steps may be implemented in hardware, in software or in a combination thereof. Implementation in hardware may include a suitably programmed FPGA (field-programmable-gate-array) or a hardwired IC chip. For good responsiveness and high throughput, multi-core processors such as GPU or TPU or similar may be used to implement the above described training and use of the machine learning model, in particular for NNs.

The components of the image processing system SYS may be implemented as software modules or routines in a single software suit and run on a general purpose computing unit PU such as a workstation associated with the imager IA, IA2 or a server computer associated with a group of imagers. Alternatively, the components of the image processing system IPS may be arranged in a distributed architecture and connected in a suitable communication network. In the alternative, or in addition, some or all components of system SYS may be arranged in hardware such as a suitably programmed FPGA (field-programmable-gate-array) or as hardwired IC chip.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system (SYS) for supporting a medical procedure, comprising:
    an interface (IN) configured to receive at least one medical input signal that describes a state of a target anatomy, wherein the medical input signal includes:
        i) a medical image of the target anatomy acquired by an imaging apparatus (IA), and
        ii) a physiological signal of the target anatomy acquired by a measuring device (PR); and
    a signal analyzer (SA) configured to analyze the medical image and the physiological signal to determine a time window for deployment of a cardiovascular device (CL) to be deployed by a deployment device (CAT) in relation to the target anatomy.

2. System of claim 1, comprising a controller (CON) configured to issue, based on the determined time window, a control signal to affect operation of the deployment device.

3. System of claim 2, wherein the control signal is operable to transition the deployment device (CAT) between at least two states, including a release state in which the cardiovascular device (CL) is deployable, and a retain state, in which the cardiovascular device (CL) is not deployable.

4. A deployment device (CAT) for deploying a cardiovascular device at a target anatomy, the deployment device capable of transitioning between at least two states, including a release-state in which the cardiovascular device is deployable, and a retain state, in which the cardiovascular device is not deployable, the deployment device including an interface (IF) configured to enable or disable the transitioning in response to a control signal issued by the controller of a system according to claim 2.

5. The deployment device of claim 4, further including a manual interface (MUI) operable by a user to issue a manual control signal in an attempt to effect the transitioning, wherein the or a control signal issued by the controller (CON) blocks, at least temporarily, or delays, the manual control signal, if the manual control signal is received outside the deployment window.

6. System of claim 1, the system further comprising an output interface (OUT) for providing a sensory indication on whether or not the deployment time has been so determined.

7. System of claim 1, wherein the medical image is any one or more of a MRI, X-ray or ultrasound image, and/or wherein the physiological signal is an ECG signal.

8. System of claim 1, wherein the cardiovascular device (CL) includes any one or more of: i) a mitral clip, ii) a replacement heart valve, and/or wherein the deployment device (CAT) includes a catheter and/or a robotic device.

9. System of claim 1, wherein the signal analyzer (SA) includes a pre-trained machine learning component (MLC).

10. System of claim 1, wherein the signal analyzer (SA) is configured to analyze the medical image so as to find an instance of a desired geometrical or mechano-geometrical configuration between the cardiovascular device to be deployed and the target anatomy.

11. An arrangement (AR) comprising: the system (SYS) as per claim 1, at least one apparatus (IA, PR) to measure the medical input signal; and the deployment device (CAT) for deploying a cardiovascular device at a target anatomy.

12. A computer-implemented method for supporting a medical procedure, comprising:
    receiving (S610) at least one medical input signal that describes a state of a target anatomy, the medical input signal including i) a medical image of the target anatomy acquired by an imaging apparatus (IA), and ii) a physiological signal of the target anatomy acquired by a measuring device (PR); and
    analyzing (S620) the medical image and the physiological signal to determine a time window for deployment of a cardiovascular device (CL) to be deployed by a deployment device (CAT) in relation to the target anatomy.

13. A computer program element, which, when being executed by at least one processing unit (PU), is adapted to cause the processing unit (PU) to perform the method as per claim 12.

14. A computer readable medium having stored thereon the program element of claim 13.

* * * * *